United States Patent
Abou Saleh et al.

(10) Patent No.: US 7,470,402 B2
(45) Date of Patent: Dec. 30, 2008

(54) AUTOMATIC PRECISION PIPETTING DEVICE

(75) Inventors: Khaled Abou Saleh, Courbevoie (FR); Alain Rousseau, Paris (FR)

(73) Assignee: Stago Instrument, Gennevilliers (FR)

( * ) Notice: Subject to any disclaimer, the term of this patent is extended or adjusted under 35 U.S.C. 154(b) by 721 days.

(21) Appl. No.: 10/505,261

(22) PCT Filed: Feb. 13, 2003

(86) PCT No.: PCT/FR03/00457

§ 371 (c)(1), (2), (4) Date: Aug. 20, 2004

(87) PCT Pub. No.: WO03/073108

PCT Pub. Date: Sep. 4, 2003

(65) Prior Publication Data

US 2005/0079073 A1 Apr. 14, 2005

(30) Foreign Application Priority Data

Feb. 25, 2002 (FR) .................................. 02 02379

(51) Int. Cl.
*B01L 3/02* (2006.01)
*B67D 5/34* (2006.01)
*B67D 5/52* (2006.01)

(52) U.S. Cl. ................. 422/100; 73/863.01; 73/863.02; 73/864.15; 73/864.17; 137/613; 137/614.11; 422/67

(58) Field of Classification Search .................. 422/67, 422/100; 73/863.01, 863.32, 864.01, 864.11, 73/864.15, 864.17; 137/613, 614.11
See application file for complete search history.

(56) References Cited

U.S. PATENT DOCUMENTS

| 3,572,130 A * | 3/1971 | Goldsmith ............... 73/864.12 |
| 3,666,420 A * | 5/1972 | Paatzsch ....................... 422/81 |
| 3,800,984 A * | 4/1974 | Phelan ........................ 422/100 |
| 3,810,720 A | 5/1974 | Lartigue et al. |
| 4,476,095 A | 10/1984 | Scott et al. |
| 4,729,876 A * | 3/1988 | Hennessy et al. ............ 422/103 |

(Continued)

FOREIGN PATENT DOCUMENTS

EP 0 070 571 A2 1/1983

(Continued)

*Primary Examiner*—Jill Warden
*Assistant Examiner*—Cedric A Chan
(74) *Attorney, Agent, or Firm*—Browdy and Neimark, P.L.L.C.

(57) ABSTRACT

The invention relates to an automatic precision pipetting device. The inventive device comprises at least two cylinder/piston-type pumping units (1, 2), the rods of which are rotated by means of a common motor unit (MP). Moreover, the pumping chamber of each of the pumping units (1, 2) is connected to a circuit comprising, successively, a conduit that opens into a container of rinsing liquid (RL), three successive solenoid valves ($EV_1$, $EV_2$, $EV_3$) and a portion of circuit which connects the second solenoid valve ($EV_2$) with the pipetting means (AP). The larger pumping chamber is connected in the part of the circuit that provides the connection between the two solenoid valves ($EV_1$, $EV_2$) while the second pumping chamber is connected to the above-mentioned portion of circuit by means of a connector, said portion of circuit comprising a solenoid valve ($EV_3$) which is disposed between said connector and the aforementioned pipetting means. The invention is suitable for reagent reconstitution, in particular, in an automatic analysis device.

16 Claims, 5 Drawing Sheets

U.S. PATENT DOCUMENTS

| | | | |
|---|---|---|---|
| 4,926,701 A | 5/1990 | Tompkins | |
| 5,474,744 A | 12/1995 | Lerch | |
| 6,405,609 B1 * | 6/2002 | Richards et al. | 73/864.14 |
| 6,555,065 B1 * | 4/2003 | Melet | 422/73 |

FOREIGN PATENT DOCUMENTS

| | | |
|---|---|---|
| EP | 0 569 213 A1 | 10/1993 |
| FR | 2 815 719 | 4/2002 |

\* cited by examiner

AUTOMATIC PRECISION PIPETTING DEVICE

The present invention concerns an automatic precision drawing-off device with rinsing of the pipette, this device making it possible to restore reactive agents and being able to be used in an analysis robot.

It more particularly concerns a device of this type having a modular structure enabling it to be easily adapted according to the required precision and specifications, both as regards the quantities of products sampled in the pipette as well as the quantities of rising liquid used.

Generally speaking, there already exist a large number of devices able to carry out drawing-off and rinsing cycles, especially inside an automatic analysis device.

Usually, these devices introduce at least two motorisations, one being used to activate a doping syringe, the other being used to drive in rotation a pump used for injecting rinsing liquid. In fact, the doping syringe, which is provided for small liquid quantities, has an insufficient capacity to carry out rinsing.

This solution is thus relatively complex and expensive. It introduces a pump whose motorisation is expensive in terms of energy and whose fragility and period of life are not as good as those of the syringe. The reliability of the unit is therefore not one would hope to expect. Now, this type of device needs to be able to function without the need for maintenance for at least seven years at the cycle of the robot on which it is used. In the case of a robot such as the one described in the patent FR 2 779 827, this rate is 60 tests per hour for at least two hours per day 220 days a year (namely about 185,000 tests).

Now it has been observed that the mechanism for activating the syringe is the centre of wear generating in the long run an increasingly larger play. This is particularly the case when this mechanism comprises a back-geared motor coupled to the rod of the syringe by means of a device for converting the movement of rotation of the motor into a linear movement of said rod. The play is then due to the wear of the teeth of the pinions and/or of the racks used both in the back-geared motor and in the conversion device.

Of course, the accuracy of the drawing-off device is affected by this play which acts in the way of a hysteresis so as to limit the travel of the rod of the syringe at its two extremities. This play appears more particularly on each inversion of the direction of rotation of the motor. It is that much more harmful to the accuracy of the device when digital data relating to the quantities of liquid picked up by the pipette are provided by a digital encoder equipping the motor and as a result, the mechanical play induces a difference between the volume determined according to the data provided by the encoder and the volume of liquid effectively picked up or put back by the pipette.

Moreover, so as to embody a drawing-off device whose reliability and period of life are the same as those of the drawing-off syringe, the Applicant has embodied a drawing-off device comprising at least two pumping units, each comprising a cylindrical cavity inside which a rod/piston assembly slides imperviously, said assembly delimiting with the cavity a working chamber whose volume varies according to the axial position of the rod/piston assembly.

The extremities of the two rods/pistons coming out of two cavities are coupled to an activation member driven in translation by a common motorisation.

The working chamber of each of the pumping units is moreover connected to a circuit successively comprising a pipe opening into a liquid rinsing reserve, two successive electrovalves and a tube, possibly flexible, connected to drawing-off means, such as a needle.

The largest working chamber is then connected into the circuit portion ensuring the joining point between the two electrovalves, whereas the other working chamber is connected into the circuit portion situated between the second electrovalve and the drawing-off means.

This device further comprises means for controlling the motorisation and electrovalves designed so as to provide a cycle comprising at least:

- a drawing-off phase in which the first electrovalve is open, the second electrovalve is closed and the motorisation drives in translation the two rod/piston assembles so as to increase the volume of the two working chambers, the volume increase of the small chamber generating the sucking up of the liquid to be analysed or sucking up of the reactive agent in the drawing-off means, whereas the volume increase of the large chamber provokes sucking up of the rinsing liquid inside this chamber,
- a flow back phase in which the two electrovalves are in the same state as during the drawing-off phase, the motorisation then acting so as to provoke a reduction of the volumes of said working chambers and a flowing back of the reactive agent or the liquid to be analysed,
- a rinsing phase in which the first electrovalve is closed whereas the second is open, the motorisation driving in translation the two rod/piston assemblies so as to reduce the volume of the two working chambers by expelling the rinsing liquid they contain towards the drawing-off means.

So as to eliminate the drawbacks due to mechanical plays, the invention provides an additional electrovalve placed in the circuit connecting the second pumping unit to the pipette and only opens this electrovalve so as to only carry out the sampling phase and/or flow back phase when the rod/piston assemblies are currently moving in either direction after the inversion or starting transitory phases and/or stoppage the transitory phases.

By means of this disposition, the teeth of the pinions and the racks of the kinematic chain, which mutually gear, are firmly in support against one another and thus the mechanical play (even if it exists) does not appear during these periods.

Of course, the device of the invention could comprise a number n of pumping units whose rod/piston assemblies are connected to a given activation member and whose working chambers are respectively connected to a circuit comprising a number n of electrovalves in series respectively connected in the circuit portion ensuring the joining points between the electrovalves concerning the n−1 first valves, the small working chamber from the nth valve being connected to the drawing-off means by means of a circuit comprising an n+1$^{st}$ electrovalve. Said control means are then designed so that in each of said phases a specific number i of electrovalves are found in a closed state, whereas the other valves, namely a number n-i, are found in the open state.

Advantageously, the device of the invention could comprise a plurality of modules each comprising one pumping unit of the above-mentioned type whose working chamber is connected to a circuit portion comprising one electrovalve. This circuit portion then comprises at each of its extremities means for connecting to the circuit portion of another module and/or to the pipe opening into the rinsing liquid reserve and/or to the tube connected to the drawing-off means. The coupling means between the motorisation and the rod/piston assemblies are then designed to allow coupling of the number of the desired modules.

Embodiments of the invention are described hereafter and given by way of non-restrictive examples with reference to the accompanying drawings in which.

Figure 1:
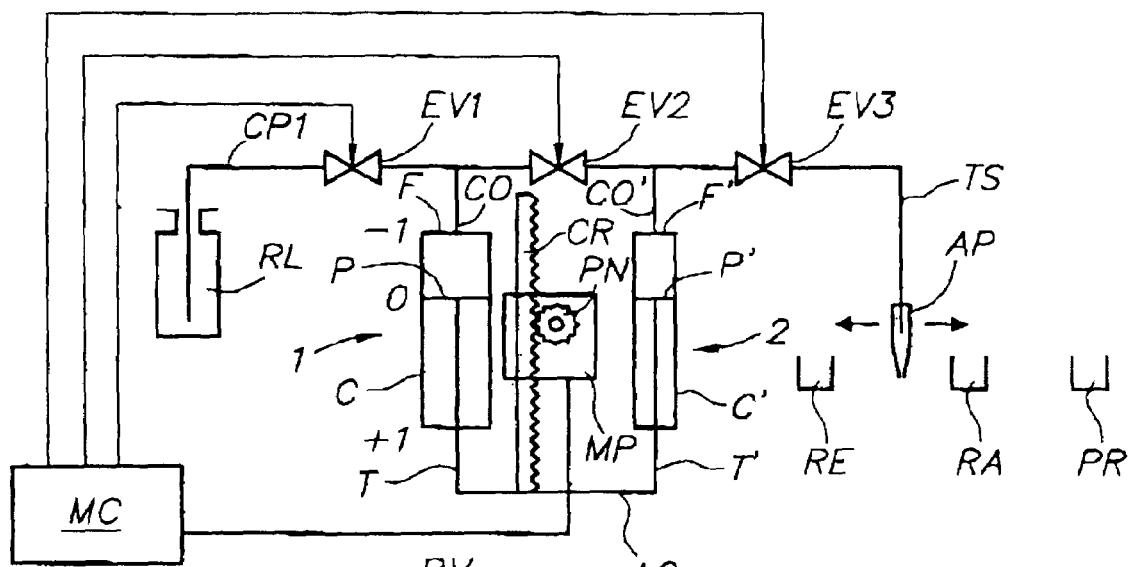
FIG. 1 is a skeleton diagram of a drawing-off device according to the invention and using two syringes.

In the example shown on FIG. 1, the drawing-off device comprises two pumping units 1, 2 each comprising a cylindrical body C, C' in which a piston P, P' move, said body delimiting with a bottom F, F' a working chamber with a variable volume.

This piston is integral with a rod T, T' coming out of the body on the side opposite the bottom F, said rod being coupled to a translation activation mechanism introducing:

a coupling element AC to which the rods T and T' are secured (there is play between T, T' and AC so as to mitigate the parallelism defects), a rack CR integral with the coupling element AC which extends parallel to the axis of the cylindrical bodies C, C', a pinion PN driven by a step motor MP which gears with the rack CR.

The bottom of each of the bodies C, C' is provided with a pipe CO, CO' making the corresponding working chamber communicate with a circuit comprising in series a pipe CP1 opening into a liquid rinsing reserve RL, three successive electrovalves $EV_1$, $EV_2$ and $EV_3$ and a flexible tube TS connecting the electrovalve $EV_3$ to a mobile drawing-off needle AP.

This needle AP is activated so as to be able to be engaged in various receptacles, such as a reserve RE containing a sample or reactive agent, an analysis receptacle RA and a rinsing well PR.

More specifically, the pipe CO is connected to the circuit connecting the electrovalves $EV_1$, $EV_2$. The pipe CO' opens into the circuit portion ensuring the link between the electrovalve $EV_2$ and the electrovalve $EV_3$.

Control of the electrovalves $EV_1$, $EV_2$, $EV_3$ and the motor MP is provided by a microcontroller MC, an optical sensor providing the "zero" position of the system.

Figure 2:
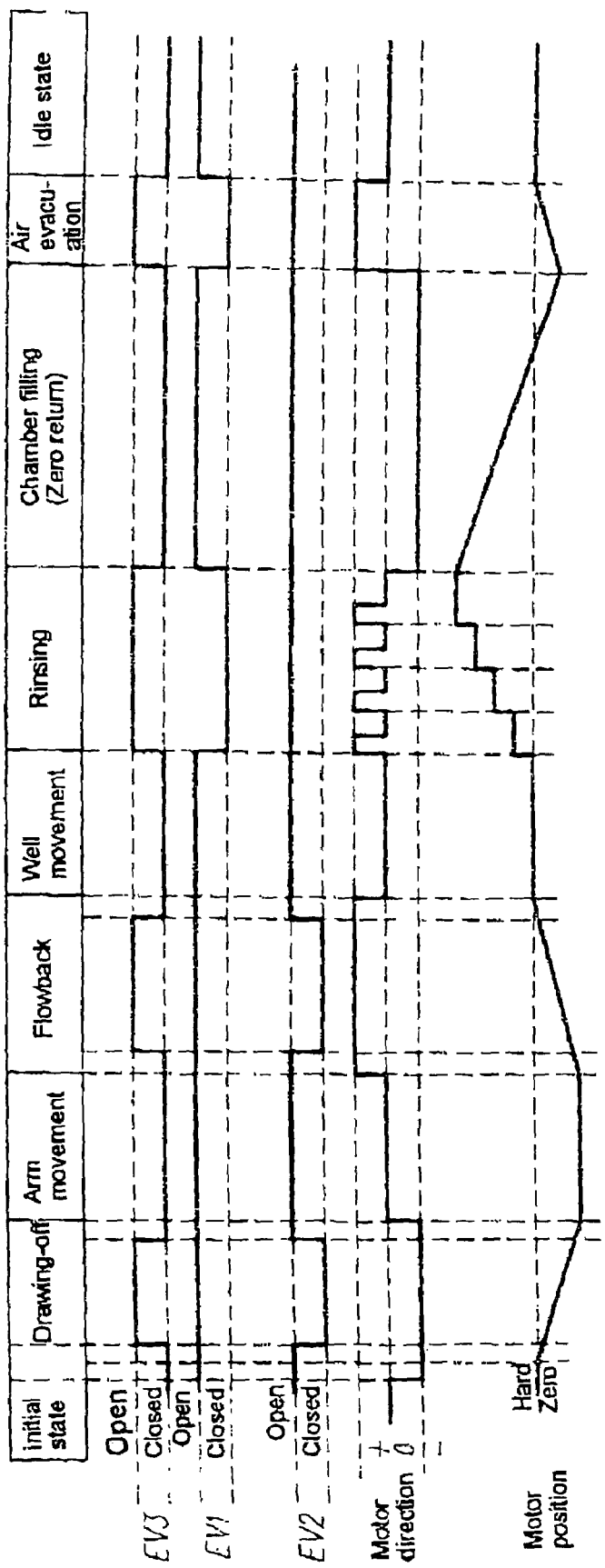
FIG. 2 is a timing diagram of a complete operating sequence of the drawing-off device shown on FIG. 1.

The functioning of the drawing-off device previously mentioned is described hereafter with reference to the timing diagram of FIG. 2.

According to this timing diagram, in an initial state, the needle AP is engaged in the reserve RE, the valves $EV_1$, $EV_2$ are located in an open position whereas the valve $EV_3$ is in a closed position. The motor MP is at a dead stop, the pistons being in the idle position (position 0). The two working chambers of the pumping units 1, 2 are filled with rinsing liquid.

During a transitory phase preceding drawing-off, the motor MP is driven in rotation in a negative direction so as to move the two pistons P, P' downwards. This movement creates a sucking up of the rinsing liquid into the two working chambers. The incidence of the play present in the kinematic chain (which provokes a slight shift in suction) has no effect on the functioning of the device.

The drawing-off phase is then obtained by closing the valve $EV_2$ and by opening the valve $EV_3$. In this case, the piston P' creates suction of the liquid contained in the reserve RE, inside the needle AP and a portion of the flexible tube TS, whereas the piston P sucks up the rinsing liquid contained in the reserve RL.

At the end of drawing-off, the device moves through a second transitory phase marked by the closing of the valve $EV_3$ and the opening of the valve $EV_2$ so that drawing off is ended whereas the motor, which continues to rotate, provokes suction by the two chambers of the rinsing liquid derived from the receptacle RL.

At the end of this second transitory phase, the motor MP is stopped and the needle AP is moved for example, so as to be located above the analysis receptacle RA.

Once this position is reached, the device starts a third transitory phase in which the motor MP rotates in an opposite direction (positive direction) so as to drive the pistons P, P' towards their idle positions (position 0). During this transitory phase, the valve $EV_3$ remains closed is whereas the valves $EV_1$ and $EV_2$ are open so as to allow a flowing back of the rinsing liquid towards the receptacle RL.

The flowing back phase is then initiated by opening the valve $EV_3$ and by closing the valve $EV_2$, the valve $EV_1$ staying open. During this phase, the piston P' pushes back the liquid previously sampled in the needle AP inside the receptacle RA, whereas the piston P pushes back the rinsing liquid inside the receptacle RL.

The flowing back phase ends by the closing of the valve $EV_3$ and the opening of the valve $EV_2$, the valve $EV_1$ remaining open.

The motor continues to rotate during a fourth transitory phase and then is stopped.

The device then starts a phase during which the needle AP is brought to the right of the rinsing well to allow execution of a rinsing phase.

At the start of this new phase, the valve $EV_1$ is closed, whereas the valves $EV_2$ and $EV_3$ are open. The motor MP is activated so as to push back the rinsing liquid contained in the two syringes in the direction of the drawing-off needle.

In fact, this flowing back is carried out in several stages each corresponding to one or several steps of the motor MP.

Once the rinsing phase is carried out, the device starts a return to zero phase with filling of the chambers with the rinsing liquid. To this effect, the valves $EV_1$ and $EV_2$ are open whereas the valve $EV_3$ is closed. The motor rotates in an inverse direction (negative direction) so as to bring the pistons back slightly beyond the idle position (position 0) by sucking up the rinsing liquid derived from the receptacle RL.

The device then proceeds to a phase for evacuating air from the needle AP by opening the valves $EV_2$ and $EV_3$ and by closing the valve $EV_1$ and by making the motor MP rotate in a positive direction so as to provoke a flowing back of the rinsing liquid towards the drawing-off needle AP and bring the piston and $TP_2$ into an idle position.

Once this air evacuation phase has been completed, the device goes back to its idle position. The electrovalve $EV_3$ is then closed, whereas the electrovalves $EV_1$ and $EV_2$ are opened.

The device is then ready to conduct a new operating cycle.

Figure 3:
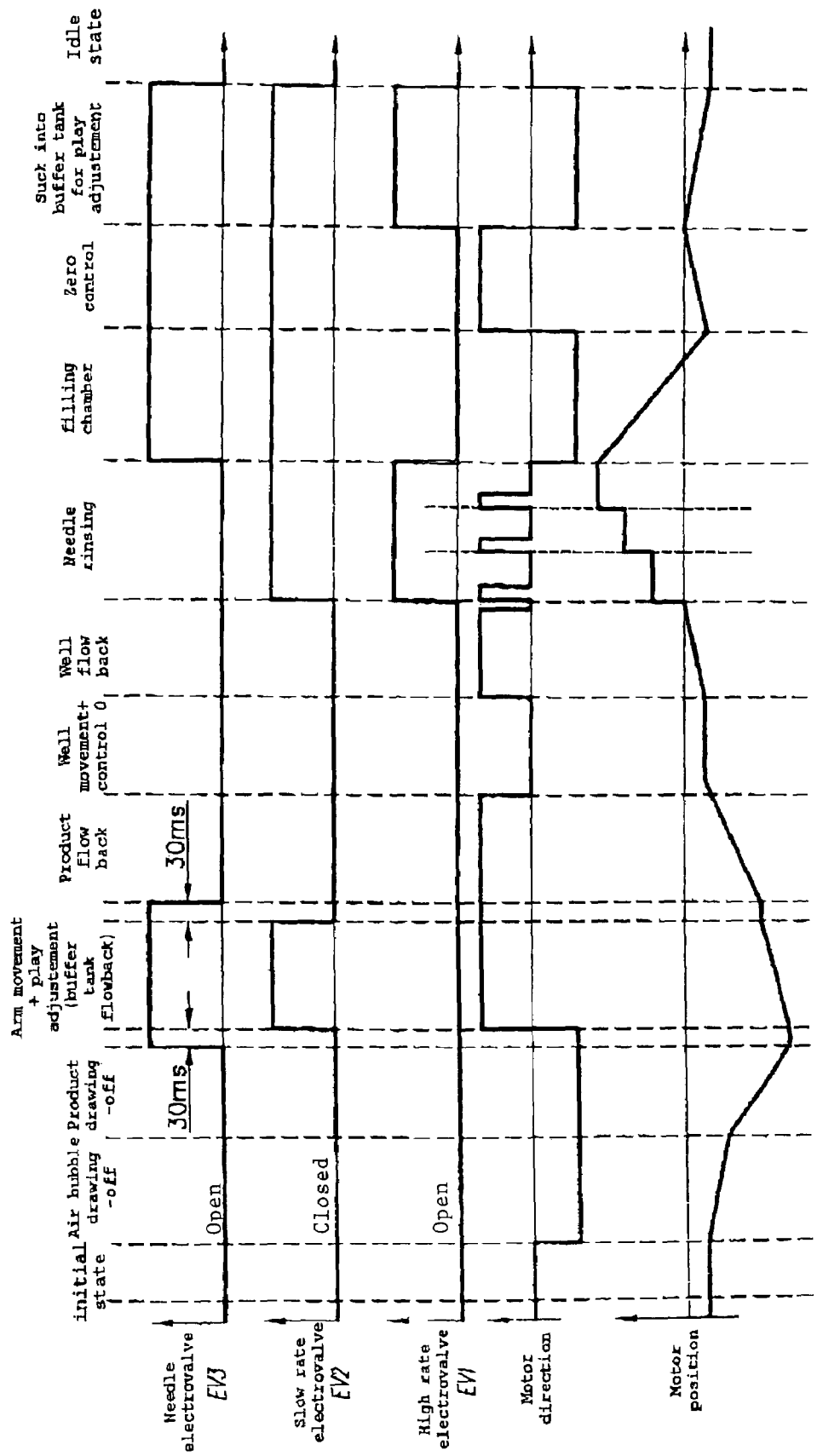
FIG. 3 is the timing diagram of a simplified operating sequence variant of the drawing-off device shown on FIG. 1.

In the simplified sequence shown on FIG. 3, in an initial state the valves $EV_1$ and $EV_3$ are open whereas the valve $EV_2$ is closed. In fact, this concerns the idle positions (non-excited state) of these valves. The motor is at a dead stop and its angular position is situated slightly below its zero position.

From this initial state, the motor is driven in rotation in a negative direction so that the piston P' generates suction inside the pipette (drawing off of an air bubble), whereas the piston P generates a suction of the rinsing liquid present in the reserve RL.

The pipette is then engaged in the reactive agent reserve whereas the rotation of the motor in a negative direction is accelerated. A drawing-off phase is then obtained which shall continue for a predetermined period during which the reactive agent is sucked up into the pipette via the action of the piston P'. This drawing-off phase ends by stoppage of the motor, the closing of the valve $EV_3$ and then of the valve $EV_2$ 30 ms later. The motor starts a transitory phase for inverting the direction of rotation lasting for a relatively short period.

The rinsing liquid, pushed back by the pistons, then returns to the reserve RL.

Once adjustment of play has been completed, the valve $EV_2$ is closed and the valve $EV_3$ is opened 30 ms later.

The pipette is then moved so as to be brought to the right of the analysis receptacle RA. Once this position is reached, the device starts a phase for pushing back the product into the analysis receptacle RA, rotation of the motor being accelerated in a positive direction. This flowing back phase ends by stopping the motor.

The pipette is then brought to the right of the rinsing well, whereas a control is carried out of the zero position of the motor.

The motor is then driven in a positive direction so as to push back the liquid contained in the pipette into the well.

The device then starts a rinsing phase in which the valves $EV_2$ and $EV_3$ are open whereas the valve $EV_1$ is closed.

During this phase, the motor caries out a succession of movements of rotation in a positive direction so as to obtain a flowing back in several stages each corresponding to one or several steps of the motor.

At the end of rinsing, the valve $EV_3$ is closed whereas the valves $EV_1$ and $EV_2$ are opened. The motor is driven in rotation in a negative direction so as to provoke a suction of the rinsing liquid by the pistons P and P'. This phase is continued until the position of the motor is slightly below the zero level.

This device then starts a zero control phase during which the motor is driven in rotation in a positive direction until the zero position is detected.

The valve $EV_1$ is closed again and the motor is driven in rotation in a negative direction until the motor returns to a position situated slightly below the zero level (play adjustment).

The cycle is then ended and the device returns to its initial state, the valves $EV_1$ and $EV_3$ being open, the valve $EV_2$ closed and the motor MP being at a dead stop.

Advantageously, the previously described device could be dimensioned so as to be able to be compatible with currently used analysis robots.

By way of example, in this device used on a robot, such as the one described in the document FR 2 779 827:

- the minimum volume to be drawn off could be equal to 5 µl, the maximum volume equal to 250 µl, (this volume being determined by adjusting the number of steps of the motor during the suction and flowing back phases)
- for the reactive agent restoration function, the maximum volume to be drawn off could be equal to 8 ml,
- the starting flowrate could be 24.4 µl/s or 73.2 µl/s, the upper flowrate being about 366 µl/s.
- the device could be able to carry out 10 successive rinsings with a volume of 150 µl with a period of 100 ms per rinsing, the pressure of the rinsing stages could be 3 bars,
- the motor MP used may consist of a step backgeared motor comprising 200 steps per rotation,
- the diameter of the piston of the body of the drawing-off unit 1 could be equal to 14 mm, whereas the diameter of the piston of the body of the drawing-off unit 2 could be 3 mm,
- the length of the two bores could be 55 mm.

Figure 4:
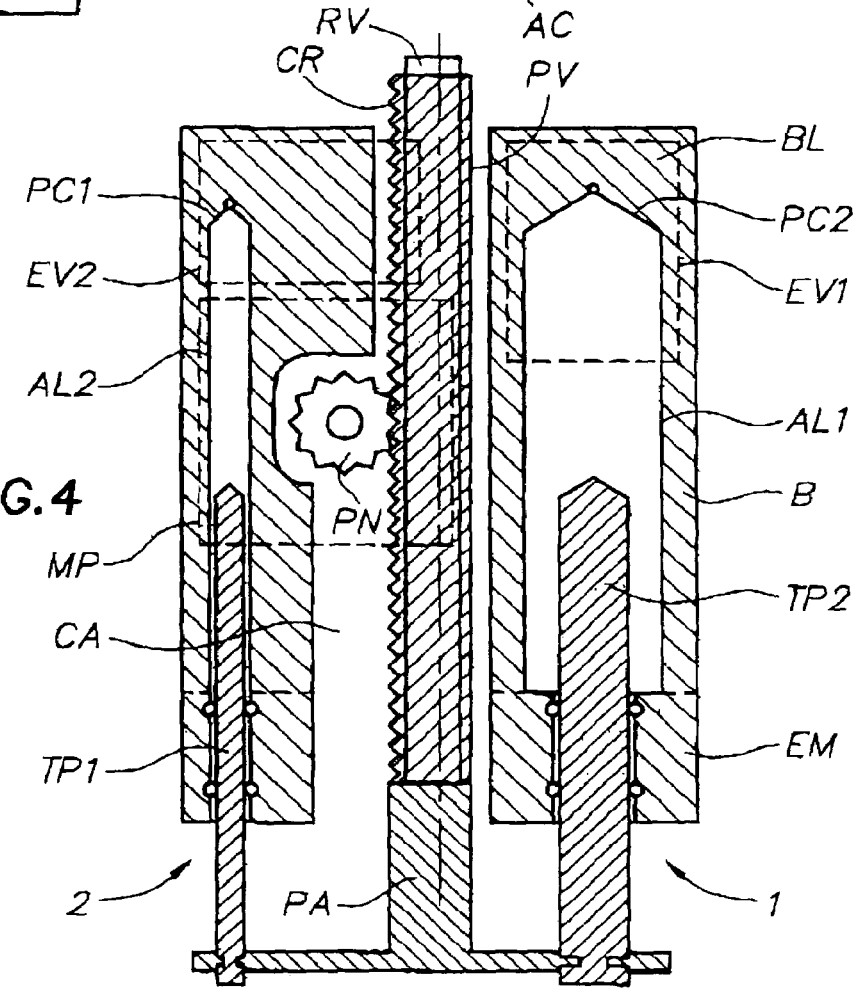
FIG. 4 is a diagrammatic cutaway view of an embodiment of the device shown on FIG. 1.
Figure 5:
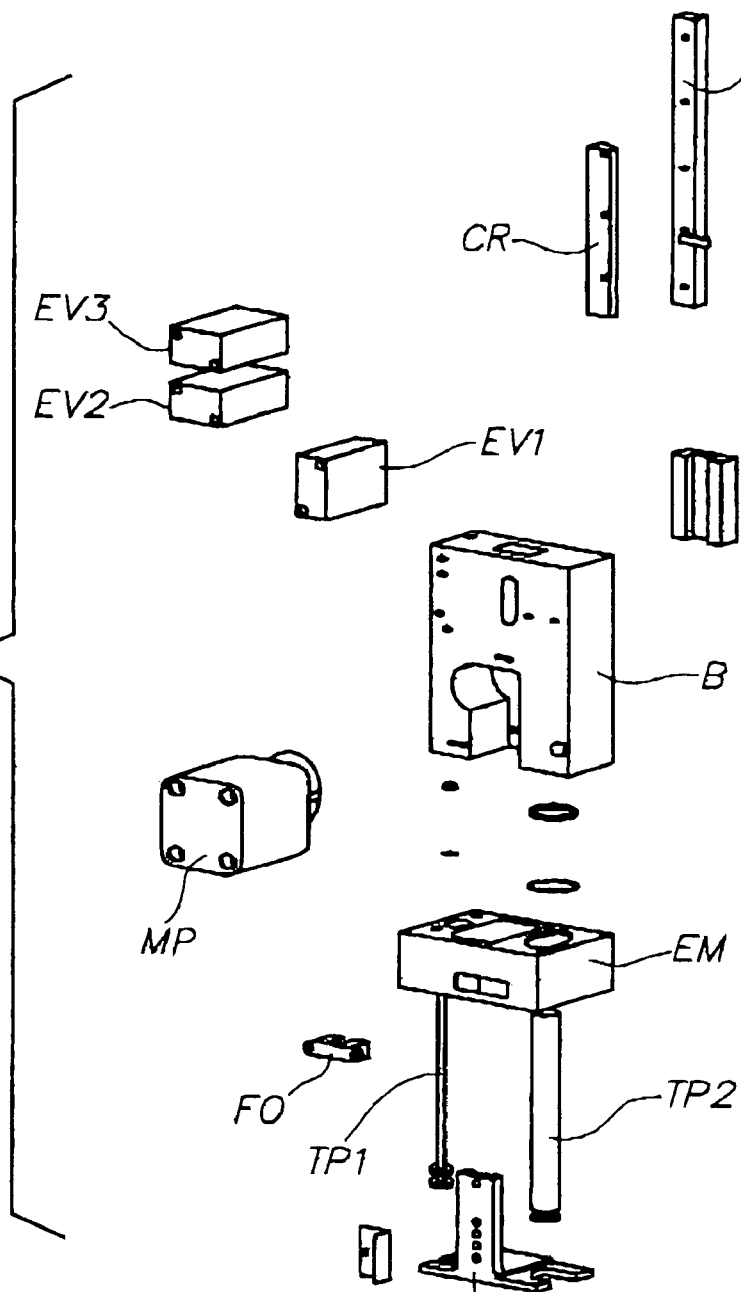
FIG. 5 is an exploded perspective view of the embodiment shown on FIG. 4.
Figure 6:
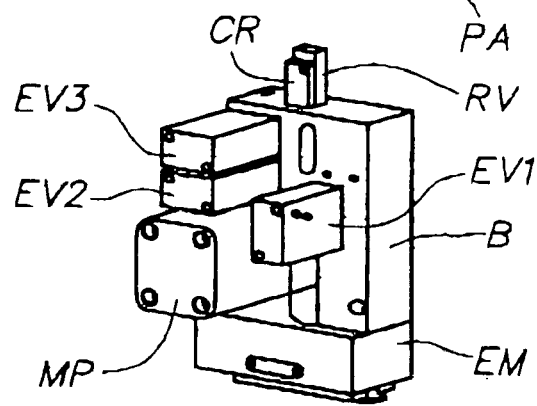
FIG. 6 is a perspective view of the device of FIG. 5 in an assembled state.

In the example shown on FIGS. 4, 5 and 6, the bodies of the two drawing-off units 1, 2 are integrated in a given plastic block BL, made for example of Plexiglas (registered trademark) having an approximately parallelepiped shape.

This body comprises two bores $AL_1$ and $AL_2$ centered parallel to the vertical axis of symmetry of the block, said bores opening outwardly at the level of the lower face of the block. In their upper portions, these two bores end by two respective conical portions $PC_1$, $PC_2$ situated at a predetermined distance from the upper face.

In the volume between the two bores $AL_1$, $AL_2$, a cavity CA is provided opening onto the lower face and onto the front face, as well as a vertical passage PV extending between the upper face of the cavity CA and the upper face of the block.

Secured to the lower face of the block is a base EM comprising two traversing vertical passages in which two respective rod/pistons $TP_1$, $TP_2$, made for example of stainless steel, are mounted sliding with imperviousness and respectively engaged in the bores $AL_1$, $AL_2$, the sliding imperviousness here being obtained with the aid of dynamic gaskets.

The upper extremities of these rods/pistons are conical, whereas their lower extremities comprise two respective throats enabling them to be fixed at the extremities of the horizontal branch of an inverted T-shaped activation element PA and also be dismantled.

The vertical branch of this activation element PA is fixed at the lower extremity of a vertical rail RV moving in vertical translation and passing into the cavity by means of an orifice provided in the base and then through the passage PV.

This rail RV bears a rack CR on which a pinion PN gears and activated by a back-geared motor (block at broken points MP) and which is located in the cavity.

Furthermore, three electrovalves $EV_1$, $EV_2$, $EV_3$ are mounted on the front face of the body in communication with pipes embodied in the bock B in accordance with the circuit shown on FIG. 1.

An optical fork FO is further provided so as to detect the "zero" position of the rail RV.

The functioning of this device is identical to that previously described and thus shall not be described again.

Nevertheless, it proves that this solution is particularly advantageous owing to its compactness, ease of integration, its aptitude for eliminating the bubbles by virtue of the conical shapes, its precision which depends on that of the rod/piston $TP_1$, $TP_2$ which can be machined with extremely high precision, and finally its reliability;

In particular, the elimination of the bubbles is due to both the conical shapes of the rod/piston $TP_1$, $TP_2$ and of the cylindrical bores $AL_1$, $AL_2$, as well as the surface state of these elements. Furthermore, the passage of the bubbles is facilitated due to the fact that the conical shape $PC_1$ of the cylindrical bore $AL_2$ with the smallest diameter communicates directly with is the pipe connected to the drawing-off means AP.

Of course, the invention is not limited to this solution.

Figure 7:
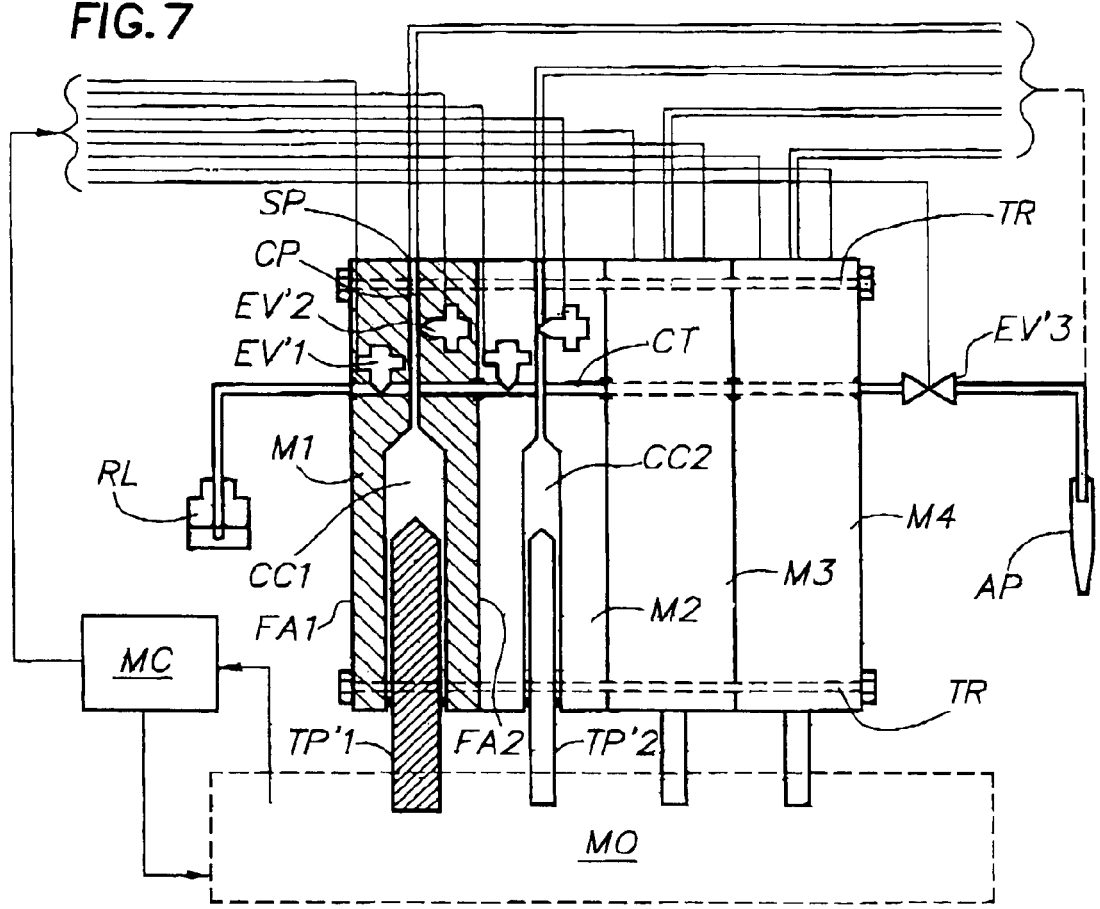
FIG. 7 is a diagrammatic section of a modular pumping unit able to be used in a drawing-off device according to the invention.
Figure 8:
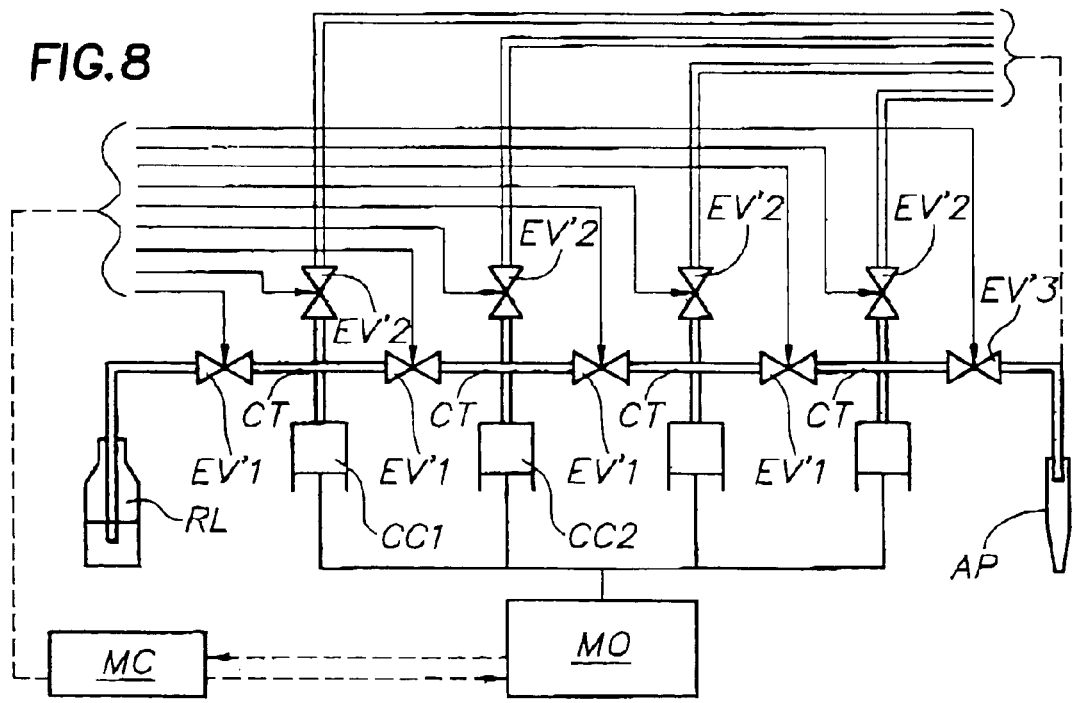
FIG. 8 is a diagrammatic representation of the pumping unit of FIG. 6.

It also concerns a modular device implementing pumping modules able to be assembled in the way indicated on FIGS. 7 and 8.

In this example, each module $M_1$ to $M_4$ comprises a cylindrical cavity $CC_1$, $CC_2$ in which a rod/piston $TP_1$, $TP_2$ is able to slide with imperviousness and activated by a motorisation (block MO) common to all the rod/piston $TP'_1$, $TP'_2$ assemblies.

This module comprises a body having two parallel assembling faces $FA_1$, $FA_2$ into which a traversing pipe CT opens in communication with the cylindrical cavity $CC_1$ and comprising a portion able to be sealed off by a punch activated by an electromagnet (the unit constituting an electrovalve $EV'_1$).

At the level of the assembling faces, the orifices of this pipe CT are equipped with connection means making it possible to provide a sealed connection of the pipe sections CT of several modules when the latter are assembled together via their assembling faces and fixed in this position, for example by tie rods TR.

In a way similar to the foregoing, the pipe obtained by the connecting of the various traversing pipes CT is connected on one side to the rinsing liquid receptacle RL and on the other side to a drawing-off needle AP by means of an electrovalve $EV'_3$.

The electrovalves $EV'_1$, $EV'_2$, $EV'_3$ and the motorisation MO are connected to a microprocessor control circuit MC.

Furthermore, each of the modules $M_1$ to $M_4$ further comprise a pipe CP in communication with the cylindrical cavity $CC_1$ and which opens onto the upper face of the module via an orifice constituting a parallel outlet SP. This pipe CP can be sealed off by a punch controlled by an electromagnet, the unit forming an electrovalve $EV'_2$ similar to the electrovalves $EV'_1$ and controlled by the control circuit.

These parallel outlets SP can be connected to the drawing-off needle AP by means of a common collector.

It is clear that this modular structure is extremely flexible and can be adapted to a large number of situations by making the number of modules vary by selecting modules having cavities with an appropriate diameter, by combining modules whose electrovalves have the same conditions, by selecting the outlets most suitable for the functions it is desired to carry out, etc. Of course, this selection can be provided by a programme implemented by the control circuit MC.

The invention claimed is:

1. Automatic precision drawing-off device comprising at least first and second pumping units having a respective first and second working chambers whose volumes vary according to the axial position of two respective rod/piston units which slide in said working chambers, said rod/piston units being coupled to an actuation member driven by a common motor, said working chambers being connected to a circuit successively comprising a pipe opening into a rinsing liquid reserve, first and second successive electrovalves and a circuit portion connecting said second electrovalve to drawing-off means, said first working chamber being connected to said circuit in a region forming a link between said first electrovalve and said second electrovalve, said second working chamber being connected to said circuit portion by means of a connector, wherein said circuit portion comprises a third electrovalve directly connected between said connector and said drawing-off means, said electrovalves and said motor being controlled by control means configured to obtain at least a drawing cycle from an initial status where the drawing-off means is engaged in a receptacle, said first and second electrovalves are open and the third electrovalve is closed, the motor is stopped, and the rod/piston units are in an idle position, wherein said control means comprises means for controlling said drawing cycle to include:

a first transitory step in which the rod/piston units are driven by said motor in a first direction to create a sucking of said rinsing liquid into the two working chambers while elements of said motor are in abutment against one another, a drawing-off phase obtained by closing said second electrovalve and by opening the third electrovalve, the two rod/piston units being moved in said first direction so that said first pumping unit sucks up the rinsing liquid contained in said reserve and the second pumping unit creates suction of the product contained in said receptacle into said drawing-off means, and a second transitory phase marked by the closure of said third electrovalve and the opening of the second electrovalve so that said drawing-off phase is ended whereas the motor continues to drive said rod/piston units in said first direction thus provoking a suction by the two chambers of the rinsing liquid derived from said reserve, the motor being stopped at the end of this second transitory phase.

2. Device according to claim 1, wherein the control means is configured to control said drawing-off cycle to include a flowing back sequence in which the rod/piston units are driven by said motor in a second direction opposite to said first direction so as to provoke a flowing back of the rinsing liquid present in the two working chambers, said control means configured to control said flowing back sequence to include the following successive phases:

a transitory phase in which the third electrovalve is closed whereas said first and second electrovalves are open so as to allow a flowing back of the rinsing liquid contained in the chambers towards said rinsing liquid reserve, a flowing back phase in which said third electrovalve is open whereas the second electrovalve is closed, the first electrovalve remaining open so as to enable the product present in said drawing-off means to flow back into an analysis receptacle, an end of flow back phase comprising the closing of said third electrovalve and the opening of the second electrovalve the first electrovalve remaining open.

3. Device according to claim 2, wherein said control means is configured to control said drawing-off cycle to include a rinsing phase during which said first electrovalve is closed whereas the second and third electrovalves are open, the motor being activated step by step so as to push back the rinsing liquid contained in the two working chambers in the direction of the drawing-off means.

4. Device according to claim 3, wherein said control means is configured to control said drawing-off cycle to include a return to said initial status with filling of the working chambers with the rinsing liquid, said first and second electrovalves being open whereas said third electrovalve is closed, the rod/piston units being driven by said motor in the first direction so as to bring back the pistons below the idle position, followed by a phase for evacuating air from said drawing-off means by opening said second and said third electrovalves and by closing said first electrovalve, said rod/piston units being driven by said motor in the second direction so as to provoke a flowing back of the rinsing liquid towards said drawing-off means and to bring back said rod/piston units into said idle position, said third electrovalve then being closed whereas said first and second electrovalves are open.

5. Device according to claim 1, wherein control means is configured to control, during said drawing-off cycle, at the time of said first transitory phase, the second and third electrovalve to open and the first electrovalve to close, and at the time of said end of said second transitory phase said third electrovalve to close and the movement of said rod/piston units to be reversed.

6. Device according to claim 5 wherein said control means is configured to control said drawing-off cycle to include a flowing back sequence with a flowing back of the rinsing liquid into the two working chambers, and secondly a flowing back of the product into the analysis receptacle, said control means configured to control this sequence to include the following successive phases:

- a phase where the first and second electrovalves are open and the third electrovalve is closed to allow a flowing back of the rinsing liquid contained in the chambers towards a receptacle,
- a transitory play adjustment phase in which the second electrovalve is closed, the first electrovalve remaining open and the third electrovalve closed,
- a phase in which the third electrovalve is open whereas the first electrovalve stays open and the second electrovalve is closed to enable the product to flow back into the analysis receptacle, and
- a phase for controlling the idle position of said rod/piston units.

7. Device according to claim 6, wherein the control means is configured to control said drawing-off cycle to include a rinsing sequence during which the liquid contained in said drawing-off means is pushed back into a rinsing well, the second and third electrovalve being open whereas said first electrovalve is closed, said motor being activated step by step so as to obtain a flowing back in several stages.

8. Device according to claim 7, wherein the control means is configured to control said drawing-off cycle to include a phase for return to an initial status comprising:

- means to control the filling of said working chambers with the rinsing liquid, the first and second electrovalves being open and said third electrovalve closed, the rod/piston units being driven in said first direction as far as a position slightly below the idle level,
- means to provide a zero control phase during which the rod/piston units are driven in said second direction until the idle level is detected,
- means to provide a play adjustment phase in which said first electrovalve is closed again and the rod/piston units are driven in the first direction until it comes back to a position situated slightly below the idle level and
- means to provide a final phase for return to an initial state in which the first and third electrovalves are open whereas the second electrovalve is closed, the motor being at a dead stop.

9. Device according to claim 1, wherein the working chambers of the two pumping units are embodied in a given material block.

10. Device according to claim 1, wherein said motor comprises a motor driving a pinion which gears with a rack integral with said actuation member.

11. Device according to claim 1, wherein the upper extremities of the working chambers and of the rod/piston assemblies are conical.

12. Device according to claim 11, wherein the conical shape of the smallest cylindrical cavity communicates directly with the circuit portion connected to the drawing-off means.

13. Device according to claim 1, wherein the said pumping units consist of modules each comprising a body having two parallel assembling faces into which a traversing pipe opens in communication with said working chambers and having one portion able to be sealed off by an electrovalve, the orifices of said pipe being equipped with connection means for providing a sealed connection with a corresponding orifice of another module when the two modules are assembled to each other via their assembling faces and fixed in this position with the aid of fixing means, said orifices being able to be moreover connected, either to a rinsing liquid intake pipe or to a pipe connected to said drawing-off means.

14. Device according to claim 13, wherein each of the modules comprises a duct in communication with said working chamber and which opens outside via an orifice constituting a parallel outlet, said duct being configured to be sealed off by an electrovalve.

15. Device according to claim 1 wherein said electrovalves and said motorisation are controlled by a processor receiving information relating to the position of the rod/piston units.

16. Device according to claim 15, which comprises an optical fork associated with said rack and connected to said processor so as to give said information.

* * * * *